United States Patent [19]

Kennedy et al.

[11] 4,070,246

[45] Jan. 24, 1978

[54] REACTIVE MATRICES

[75] Inventors: John Frederick Kennedy; Martin Frank Chaplin, both of Birmingham, England

[73] Assignee: Abbott Laboratories, North Chicago, Ill.

[21] Appl. No.: 675,110

[22] Filed: Apr. 9, 1976

[51] Int. Cl.$^2$ ............................................. G01N 33/00
[52] U.S. Cl. ...................................... 195/99; 195/101; 195/103.5 A; 260/72.5
[58] Field of Search ...................... 195/63, 68, 99, 101, 195/103.5 A, 103.5 R; 23/230 B; 424/12; 260/72.5

[56] References Cited

U.S. PATENT DOCUMENTS

| 3,794,563 | 2/1974 | Barker et al. ........................... 195/63 |
| 3,960,489 | 6/1976 | Giaever ............................... 23/230 B |
| 3,970,518 | 7/1976 | Giaever ............................... 23/230 B |
| 3,979,184 | 9/1976 | Giaever ............................... 23/230 B |

*Primary Examiner*—Raymond N. Jones
*Assistant Examiner*—C. A. Fan
*Attorney, Agent, or Firm*—Gildo E. Fato; Robert L. Niblack

[57] ABSTRACT

Compositions comprising stable, water-insoluble coatings on substrates to which biologically active proteins can be covalently coupled so that the resultant product has the biological properties of the protein and the mechanical properties of the substrate, for example, magnetic properties of a metal support. The resultant product can be utilized in diagnostic immunoassays as an example, and when the metal substrate is magnetic, the product can be removed from liquid media by a magnetic field ensuring that any washing or incubation process can be finished promptly and efficiently.

7 Claims, No Drawings

REACTIVE MATRICES

This invention relates to organic compounds, more particularly to compounds having biological or chemical activity, for example, biopolymers such as enzymes, antibodies, proteins and peptides. Such organic compounds are frequently used in chemical and biochemical reactions, and for these and other purposes it is convenient to provide them in water-soluble easily separable form. Techniques for achieving this are well known. For example, insolubilized enzymes are now firmly established as useful biochemical tools. Various insolubilization matrices have been used, such as adsorption on ion exchange materials (Gray, C.J., and Yeo, T.H., Carbohyd. Res., 27, 235 (1973)) and covalent attachment of part of the enzyme molecule to sites on a performed polymer (Barker, S.A.; Doss, S.H.; Gray, C.J.; Kennedy, J.F.; Stacey, M. and Yeo, T.H.; Carbohyd. Res., 20, 1 (1971)).

This invention relates to organic compounds in water-insoluble easily separable form on a metal substrate conveniently in the form of metal powder or of metal rods. Advantages which may result from presenting the organic compound in this form include (although not all compositions according to the invention will possess all the advantages):

a. the organic compounds can be used repeatedly;

b. the organic compound may be more stable to heat and other inactivation conditions than the corresponding free or soluble compound;

c. the composition has the properties of high density and particle size and shape imposed by the metal substrate;

d. the high density of the composition ensures that it rapidly settles out and is easily removed from suspension in aqueous and other liquid media;

e. when the metal substrate is magnetic, the speed and ease of removal of the composition from liquid media by a magnetic field ensures that any washing or incubation process can be finished promptly and efficiently, allowing a strict control over the temperature of the solution or reaction time;

f. no internal stirrer bars are necessary for performing reactions, as magnetic metal substrates can agitate solutions considerably when placed in a rotating magnetic field;

g. this process of water insolubilization of enzymes can also be used to concentrate the enzymes produced in a fermentation medium, a cellular extract, biological fluid or other aqueous fluids containing these enzymes either alone or in admixture with other compounds. Further, more than one particular enzyme or antiserum may be attached simultaneously to the metal coated support in the insolubilization. These preparations of stable water insolubilized enzymes or anti-sera on metal supports can be recovered in some instances where other insolubilized enzyme or antisera preparations are difficult or impossible to recover, such as when they are in a colloidal suspension or when other undissolved particles are present, due to their high sedimentation rate and magnetic properties;

h. by use of antisera covalently bound to metal bars, a simplified radioimmuno assay procedure is possible in which the addition and removal of the antibody (or antigen) is easily, completely and rapidly accomplished (without centrifugation) by a process that entails less skill on the part of the operator.

It is an object of the present invention to provide a stable, water insoluble coating on various metals wherein biologically active proteins can be covalently coupled such that the product has the biological properties of the protein and the mechanical and magnetic properties of the metal support.

The present invention accordingly provides a composition in which an organic compound having biological or chemical activity is carried on a metal substrate, which composition comprises:

a water-insoluble metal substrate, the surface of which is coated with an intermediate polymer, to which is coupled;

the organic compound, wherein the composition exhibits biological or chemical activity of or related to the unbound organic compound.

The metal should be one which is solid and does not react with water either in an unprotected, or if necessary a protected, state. The metal is preferably, through not essentially, magnetic, e.g., ferromagnetic; this provides advantages from some purposes, such as easy removal from liquid media, easy washing, easy automated transference and numerical counting (e.g., for packaging). The choice of metal very much depends on the conditions of the coating process. Where an acidic monomer is involved, the more electropositive metals are less satisfactory since hydrogen is generated rapidly causing disruption of the intermediate polymer surface as it is laid down. The metal may also be in modified form, e.g., embedded in some support. In the free or embedded state, the metal may be pure, impure or an alloy. In addition, "magnetic plastics" are available, and certain magnetic metal oxides, which may also be used on the metallic substrate. In all the foregoing, the metal surface may be derivatized, e.g., an oxide film.

Where it is intended to utilize the final material for competitive radio assay, it would be best to use a metal where absorption of the radiation is comparatively small. Preferred metals are aluminium, cobalt, iron, tin, and particularly nickel.

The shape of the metal substrate may be chosen to suit requirements. It will often be convenient to use metal powder. Alternatively, the metal substrate may be in the form of ferromagnetic metal bars only of which need be used at a time. These bars may be suitably shaped to avoid abrasion during stirring or, by use of a suitable magnetic filed, may be used suspended with no part touching the walls of the reaction vessel. A preferred form is that in which a metal bar is coated with a mixture of the intermediate polymer and the metal in powder form. Other possible shapes for the metal substrate include surfaces, plates, particles, spheres rods, bars and irregular shapes.

The intermediate polymer should be one which forms a continuous adherent coating on the metal substrate, and which is capable of being coupled to the organic compound. It is preferably, though not essentially, hydrophilic, and preferably, though not essentially, macroporous. It may conveniently be formed in situ on the metal substrate. When so formed, the polymer should preferably be derived from at least one acidic monomer, so as to encourage polymerization to take place on, rather than away from, the metal substrate.

While there are various ways in which the organic compound may be coupled to the intermediate polymer, the most important one is by covalent bonds resulting from chemical interaction of reactive groups on the two. Coupling of this kind is well known, and may be effected using, for example, nitrous acid, or a dialdehyde or a carbodiimide. There is a wide range of reactive groups that can be provided on the intermediate polymer for this purpose, including aliphatic amino, aromatic amino, sulfhydryl (protected if necessary), hydroxyl, aldehyde (protected if necessary) and carboxylic acid, and suitable polymers carrying these or other suitable groups can be used for the purpose of this invention. It may be possible to incorporate the reactive groups into the polymer on the metal substrate. Suitable polymers include polymers of styrene, substituted styrenes, naphthalene derivatives, acrylic and methacrylic acids, acrylamide and methacrylamide, phenol-aldehyde resins and amine-aldehyde resins, and copolymers of these with each other and with copolymerisable monomers not containing reactive coupling groups. The polymer may be used in admixture with an inert filler.

Of particular interest in this connection are polymers of aminoaromatic acids and aldehydes. Among aminoaromatic acids are preferred the 2-, 3-, and 4-aminobenzoic acids and the 2,4- and 3,5-diaminobenzoic acids, although other acids are contemplated, for example, aminobenzene sulphonic acid, tyrosine, aminosalicylic acids, glucosaminobenzoic acids, alkylformylaminobenzoic acids and related compounds such as hydroxybenzoic acids, glycine, glutamic acid and diamino benzenes and derivatives of these compounds. Among aldehydes, formaldehyde and acetaldehyde are preferred, although other mono- and di-aldehydes such as glutaraldehyde are contemplated. The use of a mixture of a mono-aldehyde and a di-aldehyde, for example, formaldehyde and glutaraldehyde may enable second aldehyde groups of the latter to remain unreacted and available for coupling with the organic compound.

The intermediate polymer may conveniently be prepared by emulsion, solution or suspension polymerization in a liquid medium (generally aqueous) containing the metallic substrate. Thus, for example, an aldehyde may be added slowly to an aqueous solution of an aminobenzoic acid containing a metallic substrate, and coated metal product recovered from the liquid. Alternatively, it may be useful to induce bead polymerization to take place around the metal as a nucleus. Materials such as dextran have been polymerized as beads, and as such offer very good matrices for immobilization. Alternatively again, the metal substrate may be coated with the preformed polymer, e.g., by dipping; this technique is likely to be particularly suitable for such polymers as cellulose and polyethylene.

Instead of coupling the organic material directly to the intermediate polymer, it may be advantageous to provide a bridge between the two. Techniques for providing such bridges are well known. One advantage of a bridge is that the organic compound may be positioned at a greater distance from the intermediate polymer and may in consequence show a greater specific activity. Another advantage is that different functional groups may thereby be attached to the intermediate polymer for coupling to the organic compound.

It is known that biopolymers may be immobilized on suitably derivatized glass. In this invention, the intermediate polymer may be a glass in the form of a coating on the metal substrate. The surface of the glass can be modified for example by there forming a diazosilane derivative or a succinimide derivative, to which the organic compound can subsequently be coupled.

A polystyrene coating may be adequate for coupling by mere adsorption, and may not therefore require chemical modification. Alternatively, the intermediate polymer may may be activated by irradiation to provide free radical sites for coupling to the organic compound. Alternatively, impregnation of the intermediate polymer with a transition metal salt may provide sites for chelate coupling with the organic compound.

This invention also provides, in a subsidiary aspect, a composition comprising a water-insoluble metal substrate, the surface of which is coated with an intermediate polymer, preferably a condensation product of an aminobenzoic acid with an aldehyde, which composition is suitable for coupling with an organic compound.

The organic material is preferably a biopolymer, that is to say a polymeric (or oilgomeric) material of biological origin or having biological activity, such as hormonal activity, antigenic activity, antibody activity, enzymic activity, or receptor activity. Biopolymers include proteins and proteinaceous materials (including glycoproteins, polysaccharide-protein complexes, immunoglobulins, enzymes); peptides and glycopeptides, polysaccharides, such as starch and dextran; and nucleic acids; and derivatives thereof. Synthetic biopolymers are becoming available, and are contemplated for use in this invention.

Other organic compounds include monomeric compounds having biological activity, and other materials that it may be desired to attach to metal substrates, for example, antibiotics, enzyme inhibitors, toxins, water-repellants and enzyme-specific ligands. The invention contemplates the use of radioactivly labelled versions of these compounds, and also of chemically or enzymatically modified forms of the compounds.

Many of these organic compounds will contain reactive groups by which they may be coupled to the intermediate polymer. For example, many of the biopolymers will contain phenolic or tyrosyl or histidinyl groups suitable for diazo-coupling, or may contain carboxyl or other groups suitable for coupling by a carbodiimide reaction. Where such groups are not present it is normally necessary to introduce suitable groups, such as aromatic hydroxyl, amino or carboxyl groups. The carbodiimide reaction is of importance because it is an example of a reaction which enables coupling to be effected without the use of acid. We have found that the use of acid in the coupling reaction can occasionally harm the properties of the intermediate polymer.

It needs to be borne in mind that modification of the organic compound, either by introducing reactive groups or by coupling to the intermediate polymer, may affect, or in some cases destroy, the chemical or biological activity that is its desired property. The skilled worker in this field will be aware of this danger; will know the portion of the organic molecule that is critical to the chemical or biological activity in question; and will seek to ensure that any modification of the organic compound does not affect this portion of the molecule. However, it is often not possible to predict whether a given organic comp und will retain its biological or chemical activity when coupled to a specific intermediate polymer on a specific metallic substrate, and a certain amount of routine experimentation in arriving at a suitable organic compound - intermediate polymer - metal substrate may therefore be inevitable. The biological or chemical activity exhibited by the composition may be less than or the same as, or greater than, the activity of the unbound organic compound.

The organic compound may be coupled to the intermediate polymer by known means. In many cases, the organic compound is dissolved or suspended in an aqueous medium and coupled to the intermediate polymer by means of nitrous acid, or glutaraldehyde, or a carbodiimide, or nitrous acid and m-diazobenzene. As is well known, nitrous acid may be formed in situ from sodium nitrite and an acid, e.g., hydrochloric or perchloric acid. Generally, the intermediate polymer will be applied to the metal substrate before being coupled with the organic compound.

After coupling with the organic meterial it will normally be desirable to block unused reactive sites on the intermediate polymer. This may conveniently be done by means of a quenching agent, for example, in the case of a diazotized aminobenzoic acid/formaldehyde polymer, a phenolic compound, e.g., 2-naphtol, or throsine, or sodium borohydride.

It is envisaged that the compositions of this invention will be used in competitive assays, for example, radioassays, particularly radioimmunoassays. The invention accordingly also procides a competitive assay kit comprising a supply of a composition as herein defined wherein the organic compound either is the compound to be assayed or a labelled version thereof. The invention also provides a method of performing a competitive assay using a composition as herein defined wherein the organic compound either is the compound to be assayed or a labelled version thereof.

When the chemical or biological activity of the organic compound is exhausted, the compound may be removed, together with the intermediate polymer, by hydrolysis and the metal substrate reused by a recoating procedure.

The following examples illustrate the invention.

Examples I to X relate to metal substrates coated with intermediate polymer.

Examples XI, XII, XIII, XVIII and XIX relate to coupling the organic compound to the intermediate polymer.

Examples XIV to XVIII demonstrate the biological activity of the bound compound.

Preparation Of Metal Coated Polymer Supports

EXAMPLE I p-Aminobenzoic acid (6 g.) was dissolved in boiling distilled water (100 ml.). Nickel powder (15 g.) was added and left in the solution for 5 minutes. Formaldehyde solution (40%, 0.1–1.0 ml.) was added to the boiling solution drop by drop. The product was filtered, ground lightly and washed several times with distilled water.

EXAMPLE II 3,5-diaminobenzoic acid was substituted for p-aminobenzoic acid in Example I.

EXAMPLE III m-Aminobenzoic acid was substituted for p-aminobenzoic acid in Example I.

EXAMPLE IV o-Aminobenzoic acid was substituted for p-aminobenzoic acid in Example I.

EXAMPLE V

Acetaldehyde was substituted for formaldehyde in Example I.

EXAMPLE VI

Cobalt powder was substituted for nickel powder in Example I.

EXAMPLE VII

Iron powder was substituted for nickel powder in Example I.

EXAMPLE VIII

Aluminium powder was substituted for nickel powder in Example I.

EXAMPLE VIIIa

Tin powder was substituted for nickel powder in Example I.

EXAMPLE IX

Nickel bars (100–200, 7.5 mm. $\times$ 2.0 mm. diam.) were substituted for nickel powder in Example I and the grinding stage omitted.

EXAMPLE X

The coated bars from Example IX were added to p-aminobenzoic acid (6 g.) in boiling distilled water and shaken moderately continuously. Nickel powder (5 g.) was added slowly until a further coat formed. The product was filtered and washed several times with distilled water.

EXAMPLE XI

Coupling of Metal Coated Enzyme Supports with β-D-glucosidase Using Nitrous Acid The metal coated enzyme support (100 mg., or one coated metal bar) was washed with distilled water (5 $\times$ 12 ml.) and added to a mixture of ice cold sodium nitrite (1.0 N., 5 ml.) and ice cold dilute hydrochloric acid (0.6–1.0 N. 5 ml.) and stirred (1–2 minutes, 0°–4° C.). The diazotised support was washed with acetate buffer (0.1 M., pH 4.8, 3 $\times$ 15 ml., 0°14 4° C.) and coupled to β-D-glucosidase (ex. sweet almonds, Koch-Light Laboratories Limited, 1–4 mg./ml.) in acetate buffer (0.1 M., ph 4.8, 1–2 mo.) for 2–18 hours at 0°–4° C. The aqueous solution we decanted and a saturated solution of β-naphthol in saturated sodium acetate (5 ml.) was added. The mixture was stirred for 2 hours (0°–4° C.). The resultant product was washed with acetate buffer (0.1 M., pH 4.8, 10 $\times$ 15 ml.) and a solution of enzyme substrate (O-nitrophenyl β-D-glucopyranoside, 1 mg./1 ml.) in the acetate buffer before use.

EXAMPLE XII

Coupling of Metal Coated Enzyme Supports with β-D-glucosidase Using Nitrous Acid and m-Diaminobenzene The metal coated enzyme support was coupled to the β-D-glucosidase as in Example XI with the addition of 2 mg. m-diaminobenzene to the hydrochloric acid before use.

EXAMPLE XIII

Coupling of Metal Enzyme Supports with β-D-glucosidase using Glutaraldehyde

The metal coated enzyme support (100 mg., or one coated metal bar) was washed with distilled water (5 × 12 ml.) and added to a solution of glutaraldehyde (2.5%, 2 ml.) and stirred (2–5 hours, 20° C.) The aqueous solution was decanted and the product washed with acetate buffer (0.1 N., pH 4.8, 5 × 12 ml.). The support was coupled to β-D-glucosidase in the acetate buffer (1 mg./ml., 2 ml., 0°–4° C, 6–18 hours). The resultant product was washed with the acetate buffer (10 × 15 ml.) before use.

EXAMPLE XIV

Activity of Bound (Metal Coated Enzyme Support) β-D-glucosidase Preparations with O-Nitrophenyl-β-D-glucopyranoside as Substrate The activity of the bound β-D-glucosidase preparations were determined by incubation (100 mg. or one coated bar) with O-nitrophenyl-β-D-glucopyranoside (1 mg./ml.) in acetate buffer (0.1 N., pH 4.8, 20° C., 1 ml.). Aliquots (0.1 ml.) were removed at various time intervals and added to a solution of sodium carbonate (0.1 N., 0.5 ml.). The absorbance at 420 nm. of the resultant solution was determined. One unit of β-D-glucosidase activity was determined to be the activity of a μg. of the unbound enzyme.

| Example | Coupling Example | Bound Protein γ g/g Solid | Enzyme Units Per g Solid | Enzyme Units Per Metal Bar |
|---|---|---|---|---|
| I | I | 1725 | 558 | — |
| I | II | — | 1100 | — |
| I | III | — | 320 | — |
| V | I | — | 100 | — |
| VI | I | — | 480 | — |
| VII | I | 1005 | 200 | — |
| IX | I | — | — | 1.0 |
| X | I | — | — | 9.0 |
| X | II | — | — | 18.5 |
| X | III | — | — | 5.0 |

EXAMPLE XV pH-Activity Relationships of Free and Bound (Metal Coated Enzyme Support) β-D-glucosidase with O-Nitrophenyl-β-D-glucopyranoside as Substrate The bound enzyme used in this experiment was that obtained from Example I using coupling Example XI. The free and bound enzymes were examined for activity at a series of pH values using the following methods:

a. Free Enzyme

The enzyme and substrate (final concentrations, 1 mg./ml. and 1 mg./ml. respectively) were incubated in the appropriate buffered solutions (see below) for 30 minutes at 20° C. An aliquot (0.1 ml.) of the reaction mixture was then added to a solution of sodium carbonate (0.1 N., 0.5 ml.) and the optical density at 420 nm. read.

b. Bound Enzyme

The metal bound - enzyme (100 mg.) was stirred in the presence of substrate (1 mg./ml., 1 ml.) in the appropriate buffered solutions (see below) for 30 minutes at 20° C. An aliquot (0.1 ml.) of the supernatant was added to a solution of sodium carbonate (0.1 N., 0.5 ml.) and the optical density at 420 nm. read:

The results are shown in Table 1.

Table 1
ACTIVITY OF FREE AND BOUND (METAL COATED ENZYME SUPPORT) β-D-GLUCOSIDASE AGAINST O-NITROPHENYL β-D-GLUCOPYRANOSIDE

| pH | Buffer | Activity (% Maximum Acivity) | |
|---|---|---|---|
| | | Free Enzyme | Bound Enzyme |
| 4.00 | Phosphate-citrate (0.1 M.) | 36 | 50 |
| 4.65 | Phosphate (0.1 M.) | 70 | 90 |
| 5.35 | Phosphate | 100 | 100 |
| 6.10 | Phosphate | 64 | 98 |
| 6.30 | Phosphate | 58 | 97 |
| 7.50 | Phosphate | 44 | 73 |
| 8.70 | Phosphate | 23 | 28 |

EXAMPLE XVI

Reuseability of Bound (Metal Coated Enzyme Support) β-D-glucosidase

Metal coated enzyme support (100 mg.) prepared as in Example 1 was coupled to β-D-glucosidase (as in Example XI). The product was repeatedly tested for β-D-glucosidase activity (as in Example XIV) using O-nitrophenyl-β-D-glucopyranoside as substrate, washing between incubations with acetate buffer (0.1 N., pH 4.8, 3 × 15 ml.).

| Activity Determination | % Original Activity |
|---|---|
| 1 | (100) |
| 2 | 103 |
| 3 | 122 |
| 4 | 124 |
| 5 | 130 |
| 6 | 127 |
| 7 | 117 |
| 8 | 132 |

EXAMPLE XVII

Heat Stability of Insolubilized β-D-glucosidase

Samples (100 mg.) of bound (metal coated enzyme support; Example I, Example XI) β-D-glucosidase and soluble β-D-glucosidase of the same order of activity were incubated at 20° C. and 37° C. and assayed as in Example IV; both soluble and insolublized enzyme were in 0.1 M. acetate buffer pH 4.8, but the incubation time for enzyme assay with respect to O-nitrophenyl β-D-glucopyranoside as substrate was 3 minutes throughout. Substrate controls were incubated simultaneously and individual assays have been corrected.

| Temperature | Time | % Activity Retention | |
|---|---|---|---|
| | | Bound Enzyme | Free Enzyme |
| 20° C. | 168 hours | 102 | 15 |
| 37° C. | 15 hours | 92 | 18 |

EXAMPLE XVIII

Coupling of Metal Coated Enzyme Supports with Antisera to Follicle Stimulating Hormone The metal coated enzyme support (100 mg., Example I) was washed with distilled water (5 × 12 ml.) and added to a mixture of ice cold sodium nitrite (1.0 N., 5 ml.) and ice cold dilute hydrochloric acid (0.6–1.0 N., 5 ml.) and stirred (1–2 minutes, 0°–4° C.). The diazotized support was washed with acetate buffer (0.1 M, pH 4.8, 3 × 15 ml., 0°–4° C.) and coupled to antisera to human pituitary follicle stimulating hormone (from rabbit blood after multiple injection with pure human pituitary follicle stimulating hormone; 4 mg./ml.) in the acetate buffer (2 ml.) for 6 hours at 0°–4° C. The aqueous solution was decanted and a saturated solution of $\beta$-naphthol is saturated sodium acetate (5 ml.) was added. The mixture was stirred for 2 hours (0°–4° C.). The resultant product was washed with acetate buffer (0.1 M, pH 4.8, 10 × 15 ml.) and tested for follicle stimulating hormone binding capacity by itself or in the presence of excess follicle stimulating hormone by the radioimmunoassay of Butt, W. R. and Lynch, S. S., Clinica. Chim. Acta 22, 79)1968).

| Bound Antisera mg. | Follicle Stimulating Hormone (FSH) Binding % | |
|---|---|---|
| | No Excess FSH | Excess FSH |
| 1 | 11.4 | 3.7 |
| 2 | 14.6 | 5.0 |
| 4 | 35.3 | 5.5 |

EXAMPLE XIX

Coupling of Metal Coated Enzyme Supports with Antisera to Follicle Stimulating Hormone Using a Water Soluble Carbodiimide The follicle stimulating hormone antiserum (10 mg.) in distilled water (1 ml.) was added to 15–20 polymer coated bars (Example IV). 1-Ethyl-3(3-dimethylaminopropyl) carbodiimide was added until the solution was 0.1 M and the pH adjusted to 5.0 with phosphate buffer (pH 4.0 or 8.0, 0.1 M) and kept at that pH for 24 hours at room temperature. The bars were washed thoroughly (10 × 15 ml.) with acetate buffer (pH 4.8, 0.1 M) after coupling.

It was demonstrated that the product of Example XVIII was capable of generating an inhibition curve in the presence of mixtures of labelled and unlabelled follicle stimulating hormone.

It has been shown above that aminobenzoic acids in aqueous solution can be used in forming the intermediate polymer. Formaldehyde, in such reactions, usually gives condensation products with the amino nitrogen under alkaline conditions but in acid it forms methylene bridges. These bridges are formed ortho-para to the aromatic amine residue and meta to the aromatic carboxylic acid.

The preferred molar ratio of aldehyde to aminobenzoic acid in the intermediate polymer is from 1:7 to 2:1. The optimum molar ratio of formaldehyde to 4-aminobenzoic acid is about 1:5 and if the formaldehyde content is increased above this, relative to the aminobenzoic acid, there is a gradual loss in enzyme coupling ability. It is believed that at low formaldehyde concentrations the predominant reaction is by methylene bridges between the aromatic rings, but as the concentration increases more of the amine functions become blocked by condensation with the excess formaldehyde. The amount of aminobenzoic acid reacted the intermediate polymer on the metal depends to a great extent on the surface area of the metal and often there is a large amount of the aminobenzoic acid left in the liquor after reaction. It is assumed that some of the formaldehyde would be reduced by the hydrogen formed by the reaction of the hot benzoic acid with the metal and in this way reduce any gas pockets which might get trapped under the forming resin matrix. It is possible that the liberated hydrogen might also reduce the amine-formaldehyde mixture to give secondary amines.

The infrared analysis of the product of Example I shows distinct differences from that of 4-aminobenzoic acid. These are most apparent in the C-H in plane deformation region (1000–1300 cm$^{-1}$) and the C-H out of plane deformation region (800–950 cm$^{-1}$), due to the change in the benzene substitution pattern, and in the N-H stretching (3300–3500 cm$^{-1}$) and deformation (1600–1650$^{-1}$) regions. There is also an appearance of a peak absorption at 1380 cm$^{-1}$ due, maybe, to the carboxylate ion. It would seem that the polymer was held to the metal by electrostatic bonds.

The polymeric matrix on the metal contained free amino groups which could be used to insolubilize enzymes through diazo coupling with enzymic tyrosine groups. $\beta$-D-glucosidase was used as an example of a typical enzyme but one which was easily obtainable and rapidly assayed.

The pH-activity profile of the bound $\beta$-D-glucosidase (Example XV) showed a broadening effect relative to the free enzyme. This effect is most evident on the alkaline side. The partial, or total, ionisation of the carboxylic acid groups would give rise to a negatively charged matrix raising the local pH of the solution above that measured for the bulk of the solution. This is a further confirmation of the electrostatic nature of the metal matrix bond.

The reuseability trail results show an initial increase in enzyme activity. This indicates that there is little or no physical adsorption of active $\beta$-D-glucosidase on the support after the routine washing procedure, but there may be an initial gradual elution of inactive $\beta$-D-glucosidase or enzyme inhibitor which was reducing the apparent activity of the matrix bound enzyme, until removed.

The effect of moderately fast magnetic stirring on the composition was to reduce its specific activity approximately 1% per hour, even in the presence of substrate. This loss is not significant in the present work where the incubations were usually only 3–5 minutes, and the loss could be reduced by less vigorous stirring. The activity loss was probably due to gradual removal of the coating by friction.

Insolubilized organic compounds have shown their usefulness in many ways. They are used where their increased stability, reuseability and recoverability relative to the unbound compound are more important than the extra work and expense of the coupling operation. They are easily recoverable from solution by simple filtration or centrifugation operations or can be used as column packings in continuous flow operations. Their repeated use offsets the higher cost of manufacture. The advantages of being able to attach organic compounds to such easily machineable metals as nickel and aluminium, as shown by the attachment of $\beta$-D-glucosidase to nickel wire and aluminium sheet, has many possible applications in the biological engineering industry, where, for example, the metal support can be in the form of small spheres for continuous flow column reactions or affinity chromatography separations, as a metal paddle in stirred reactions, or in the form of tubing for reactions involving rapid transport of material.

What we claim is:

1. A composition comprising a water-insoluble metal substrate, the surface of which is coated with a condensation product of an aminobenzoic acid with an aldehyde, which composition is suitable for coupling with an organic compound having biological activity.

2. A composition as claimed in claim 1, wherein the metal of the substrate is nickel, cobalt, iron or aluminium.

3. A composition as claimed in claim 1, wherein the metal of the substrate is ferromagnetic.

4. A composition as claimed in claim 2, wherein the metal substrate is in rod or powder form.

5. A composition as claimed in claim 1, wherein the aldehyde is formaldehyde.

6. A composition as claimed in claim 1 which is suitable for coupling with a protein.

7. A method of making the composition claimed in claim 1, which method comprises adding the aldehyde slowly to an aqueous solution of the aminobenzoic acid containing the metal substrate, and recovering the coated metal product from the liquid.

* * * * *